United States Patent
Lin

(10) Patent No.: US 8,994,936 B2
(45) Date of Patent: Mar. 31, 2015

(54) PATTERN MATCHING METHOD, APPARATUS AND LINE WIDTH MEASURING MACHINE

(71) Applicant: Shenzhen China Star Optoelectronics Technology Co., Ltd., Shenzhen, Guangdong (CN)

(72) Inventor: Yung-Yu Lin, Shenzhen (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 219 days.

(21) Appl. No.: 13/806,992

(22) PCT Filed: Nov. 27, 2012

(86) PCT No.: PCT/CN2012/085375
§ 371 (c)(1),
(2) Date: Dec. 26, 2012

(87) PCT Pub. No.: WO2014/079079
PCT Pub. Date: May 30, 2014

(65) Prior Publication Data
US 2014/0139828 A1    May 22, 2014

(30) Foreign Application Priority Data
Nov. 22, 2012 (CN) .......................... 2012 1 0477123

(51) Int. Cl.
*G01N 21/956* (2006.01)

(52) U.S. Cl.
CPC ........ *G01N 21/956* (2013.01); *G01N 21/95607* (2013.01)
USPC .................................... 356/237.5; 356/237.1

(58) Field of Classification Search
USPC ............ 356/237.1–237.5, 394; 382/149, 141, 382/154, 172, 181; 438/87
See application file for complete search history.

(56) References Cited

U.S. PATENT DOCUMENTS

| | | | | |
|---|---|---|---|---|
| 4,791,586 A * | 12/1988 | Maeda et al. | ................. | 716/112 |
| 4,805,224 A * | 2/1989 | Koezuka et al. | ............. | 382/141 |
| 5,774,574 A * | 6/1998 | Hoki | ............................ | 382/149 |
| 6,842,245 B2 * | 1/2005 | Ando | ............................ | 356/394 |
| 2006/0126934 A1 * | 6/2006 | Ichimura et al. | ............. | 382/181 |
| 2007/0258636 A1 * | 11/2007 | Kudou | ......................... | 382/149 |
| 2009/0232385 A1 * | 9/2009 | Matsuoka et al. | ............ | 382/145 |
| 2011/0158543 A1 * | 6/2011 | Morokuma et al. | .......... | 382/199 |
| 2012/0113246 A1 * | 5/2012 | He et al. | ........................ | 348/87 |

* cited by examiner

*Primary Examiner* — Sang Nguyen
(74) *Attorney, Agent, or Firm* — Andrew C. Cheng

(57) ABSTRACT

The present invention discloses a pattern matching method, which is used in measurement process for line width measuring machine, comprising: reading a standard pattern used for matching on the at least one predetermined position of a measured sample; respectively comparing each standard pattern of the measured sample with prestored multiple designed original images corresponding to the standard pattern; determining that the pattern matching is successful if the standard pattern on the measured sample successfully compares with at least one designed original image, and proceeding with the subsequent line width measurement process; otherwise, determining that the pattern matching is failed. The present invention also discloses a corresponding pattern matching method and a line width measuring machine. According to the embodiment of the present invention, it can improve the accuracy and the success rate of the pattern matching when measuring the line width.

9 Claims, 3 Drawing Sheets

PATTERN MATCHING METHOD, APPARATUS AND LINE WIDTH MEASURING MACHINE

This application claims priority to Chinese Patent Application Serial No. 201210477123.5, named as "Pattern matching method, apparatus and line width measuring machine", filed on Nov. 22, 2012, the specification of which is incorporated herein by reference.

BACKGROUND OF THE INVENTION

1. Field of the Invention

The present invention relates to a liquid crystal panel manufacturing process, and in particular to a pattern matching method, apparatus and a line width measuring machine.

2. The Related Arts

In the manufacturing process of the liquid crystal display, to determine if the coating is successful, it needs to measure the coating line width of the coated glass substrate. At the first, it needs a step of the pattern matching for the measured sample and the designed pattern to position the sample.

Generally, in order to form multiple patterns on the transparent glass substrate by coating process in the measured sample, it contains many segments in the patterns. The line width measuring machine needs to measure the width of the line segment. In order to match the patterns, at least one standard pattern used for matching is further coated at the predetermined position on the measured sample, and the patterns at different position of the standard pattern may be different. Accordingly, a designed pattern of the standard pattern is stored in the line width measuring machine (or computer), and the said pattern matching refers to comparing the standard pattern on the measured sample with a corresponding designed pattern which has been stored in advance. If the comparing result for both is the same or reaches a certain degree of similarity, the match is successful. After the successful matching, the pattern on the measured sample can be moved to the middle position to measure the line width.

However, in the prior art, once the manufacturing process of the liquid crystal panel occurs instability, it usually shows a certain degree of gray-scale on the measured sample, as shown in FIG. 1, wherein A represents the standard pattern on the measured sample, B represents the corresponding design pattern which is stored in advance, wherein the standard pattern A exists in a certain gray-scale, which differs from the designed pattern B in gray-scale. In this situation, it often leads to failed pattern matching. Actually, the differences of the gray-scale in the manufacturing process of the liquid crystal panel are acceptable. Therefore, this situation will easily lead to that the line width cannot be measured and delay the schedule.

SUMMARY OF THE INVENTION

The technical issue to be solved by the present invention is to provide a pattern matching method, apparatus, and a line width measuring machine, which improves the accuracy and the success rate of the pattern matching.

In order to solve the above technical issue, one embodiment of the present invention provides a pattern matching method, which is used in measurement process for line width measuring machine, comprising: reading a standard pattern used for matching on the at least one predetermined position of a measured sample, and the measured sample being the transparent substrate coated with multiple patterns; respectively comparing each standard pattern of the measured sample with prestored multiple designed original images corresponding to the standard pattern, and the difference within the multiple designed original images being the gray-scale; determining that the pattern matching is successful if the standard pattern on the measured sample successfully compares with at least one designed original image, and proceeding with the subsequent line width measurement process; otherwise, determining that the pattern matching is failed.

Wherein, it comprises: forming the standard pattern in advance on the at least one predetermined position of the measured sample.

Wherein, it comprises: storing the designed original image in advance from each predetermined position, the designed original image corresponding to the standard pattern on each position being a plurality, and the gray-scale corresponding to each designed original image being different.

Wherein, the step of determining that the pattern matching is successful if the standard pattern on the measured sample successfully compares with at least one designed original image specifically is: comparing the standard pattern on the measured sample with each corresponding designed original image, determining that the comparison between the measured sample on the standard pattern and the designed original image is successful if a similarity of at least one reaches a predetermined ratio, wherein the similarity reaching the predetermined ratio can be preset.

Accordingly, the embodiment of the present invention further provides a pattern matching apparatus, which is used for line width measuring machine, comprising: an image acquisition unit, which is used to read a standard pattern used for matching on the at least one predetermined position of a measured sample, and the measured sample being the transparent substrate coated with multiple patterns; a matching processing unit, which respectively compares each standard pattern of the measured sample with prestored multiple designed original images corresponding to the standard pattern, and the difference within the multiple designed original images being the gray-scale; determining that the pattern matching is successful if the standard pattern on the measured sample successfully compares with at least one designed original image.

Wherein, it further comprises: a storage unit, which is used to store the designed original image on each predetermined position, the designed original image corresponding to the standard pattern on each position being a plurality, and the gray-scale corresponding to each designed original image being different.

Wherein, the matching processing unit further comprises: an obtaining subunit, which obtains the multiple designed original images corresponding to the standard pattern on the measured sample from the storage unit; a matching sub-unit, which respectively compares the standard pattern with the multiple designed original images obtained from the obtaining subunit; a matching result judgment unit, which is used to determine that the comparison between the standard pattern on the measured sample and the designed original image is successful when the similarity between the standard pattern and one of the designed original images reaches the predetermined ratio; otherwise, determining that the comparison is failed.

Wherein, it further comprises: a setting unit, which is used to set the similarity ratio between the standard pattern and the designed original image for the determination of the matching result judgment unit.

Wherein, the measured sample is the transparent substrate coated with multiple patterns, and the patterns contain multiple segments; at least one standard pattern is further coated at the predetermined position on the measured sample.

Accordingly, the present invention further provides line width measuring machine, comprising: an image acquisition unit, which is used to read a standard pattern used for matching on the at least one predetermined position of a measured sample, and the measured sample being the transparent substrate coated with multiple patterns; a matching processing unit, which respectively compares each standard pattern of the measured sample with prestored multiple designed original images corresponding to the standard pattern, and the difference within the multiple designed original images being the gray-scale; determining that the pattern matching is successful if the standard pattern on the measured sample successfully compares with at least one designed original image; a line width measuring unit, which is used to measure the line width of the measured samples after the matching processing unit determines that the pattern matching is successful.

Wherein, it further comprises: a storage unit, which is used to store the designed original image on each predetermined position, the designed original image corresponding to the standard pattern on each position being a plurality, and the gray-scale corresponding to each designed original image being different.

Wherein, the matching processing unit further comprises: an obtaining subunit, which obtains the multiple designed original images corresponding to the standard pattern on the measured sample from the storage unit; a matching sub-unit, which respectively compares the standard pattern with the multiple designed original images obtained from the obtaining subunit; a matching result judgment unit, which is used to determine that the comparison between the standard pattern on the measured sample and the designed original image is successful when the similarity between the standard pattern and one of the designed original images reaches the predetermined ratio; otherwise, determining that the comparison is failed.

Wherein, the measured sample is the transparent substrate coated with multiple patterns, and the patterns contain multiple segments; at least one standard pattern is further coated at the predetermined position on the measured sample.

The embodiment according to the present invention has the beneficial effects as follow.

According to the embodiment of the present invention, it stores multiple designed original images for each standard pattern on the measured samples in advance, and the difference within the multiple designed original images is gray-scale; as long as the standard pattern on the measured sample successfully compares with at least one of the designed original image, determining that the pattern matching is successful. Then, it can proceed with the subsequent line width measurement process directly. In this way, it can improve the accuracy and the success rate of the pattern matching.

BRIEF DESCRIPTION OF THE DRAWINGS

In order to more clearly illustrate the embodiment of the present invention or the technical issue of the prior art, the accompanying drawings and the detailed descriptions are as follows. Obviously, the following description of the accompanying drawings are only some embodiments according to the present invention, for persons of ordinary skill in this field, they can also obtain other drawings based on these drawings without creative effort.

DETAILED DESCRIPTION OF THE PREFERRED EMBODIMENTS

The preferred embodiments of the present invention are described by the following reference to the drawings.

Figure 3:
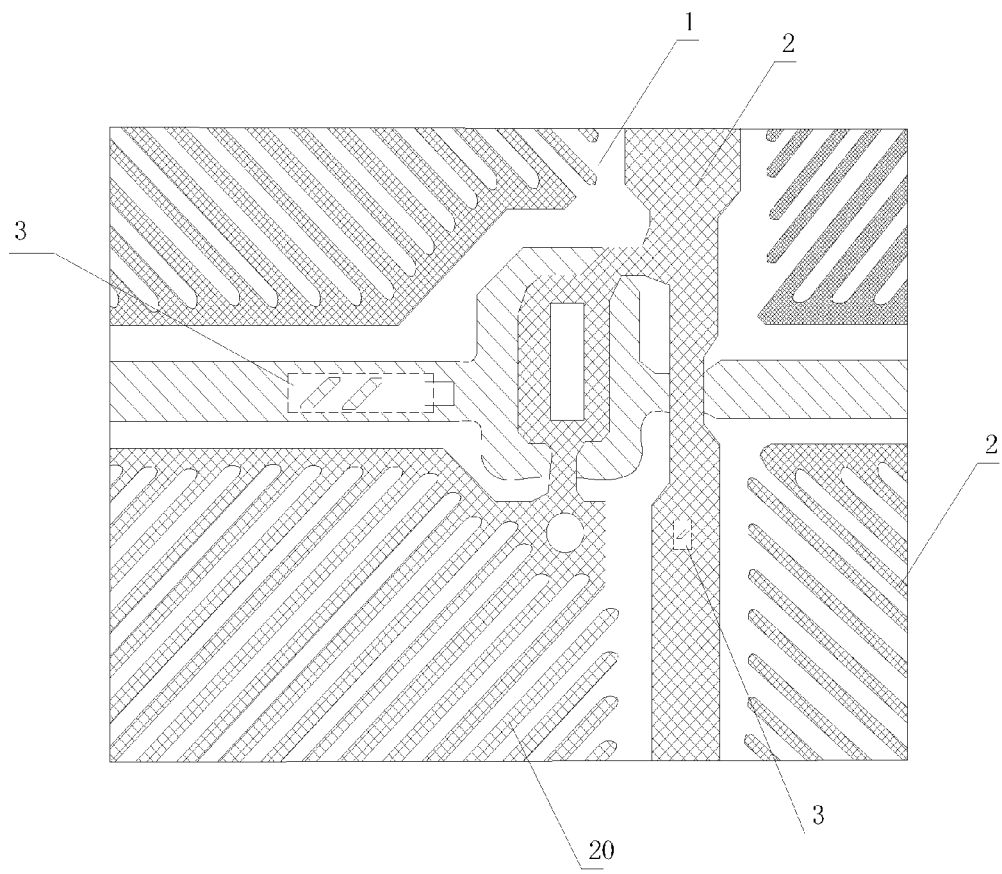
FIG. 3 is a schematic view illustrating the partial structure of the measured sample according to one embodiment of the present invention.
Figure 4:
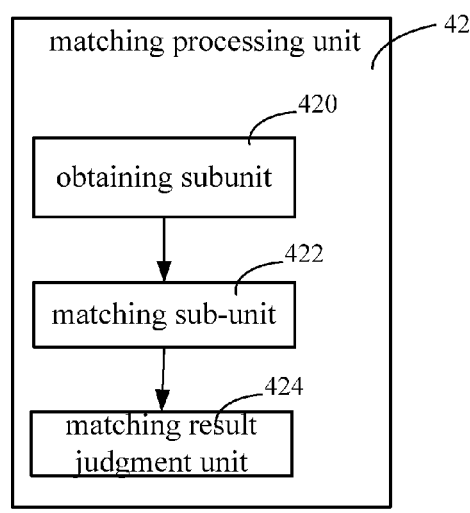
FIG. 4 is a schematic view illustrating the structure of one embodiment of the matching processing unit in FIG. 2.
Figure 5:
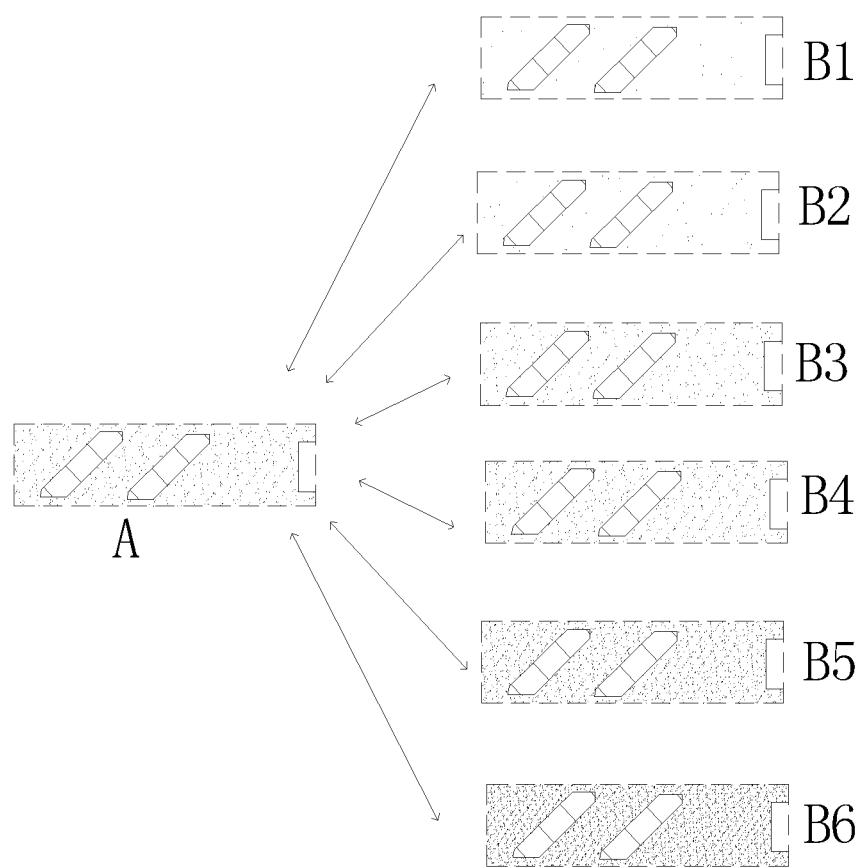
FIG. 5 is a comparison diagram between the standard pattern on the measured sample and the corresponding designed pattern according to the pattern matching of one embodiment of the present invention.

Referring to FIGS. 3 to 5, they show the line width measuring machine according to the first embodiment of the present invention. It can be seen that the line width measuring machines 4 comprises the following.

An image acquisition unit 40, which is used to read a standard pattern used for matching on the at least one predetermined position of a measured sample, and the measured sample being the transparent substrate coated with multiple patterns. The measured sample is a transparent substrate 1 coated with multiple patterns 2, and the patterns 2 contain multiple segments 20. The line width measuring machine needs to measure the width of the line segment 20. In order to matching the pattern, the standard pattern 3 is further coated at a predetermined position on the measured sample, the patterns of the standard pattern 3 at different positions may be different.

A storage unit 48, which is used to store the designed original image corresponding to the standard pattern 30 on each predetermined position. The designed original image corresponding to the standard pattern on each position is a plurality, and the gray-scale corresponding to each designed original image is different.

A matching processing unit 42, which respectively compares each standard pattern 30 of the measured sample obtained by the image acquisition unit 40 with prestored multiple designed original images corresponding to the standard pattern. The difference within the multiple designed original images is the gray-scale. Determine that the pattern matching is successful if the standard pattern on the measured sample successfully compares with at least one designed original image.

A setting unit 46, which is used to set the similarity ratio between the standard pattern and the designed original image for the determination of the matching result judgment unit 42.

A line width measuring unit 44, which is used to measure the line width of the measured samples after the matching processing unit 42 determines that the pattern matching is successful.

Wherein, the matching processing unit 42 further comprises: an obtaining subunit 420, which obtains the multiple designed original images corresponding to the standard pattern on the measured sample from the storage unit 48; a matching sub-unit 422, which respectively compares the standard pattern with the multiple designed original images obtained from the obtaining subunit; a matching result judgment unit 424, which is used to determine that the comparison between the standard pattern on the measured sample and the designed original image is successful when the similarity between the standard pattern and one of the designed original images reaches the predetermined ratio; otherwise, determining that the comparison is failed.

Figure 1:
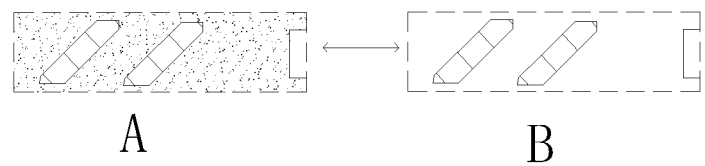
FIG. 1 is a comparison diagram between the standard pattern on the measured sample and the corresponding designed pattern according to the pattern matching in the known technology.
Figure 2:
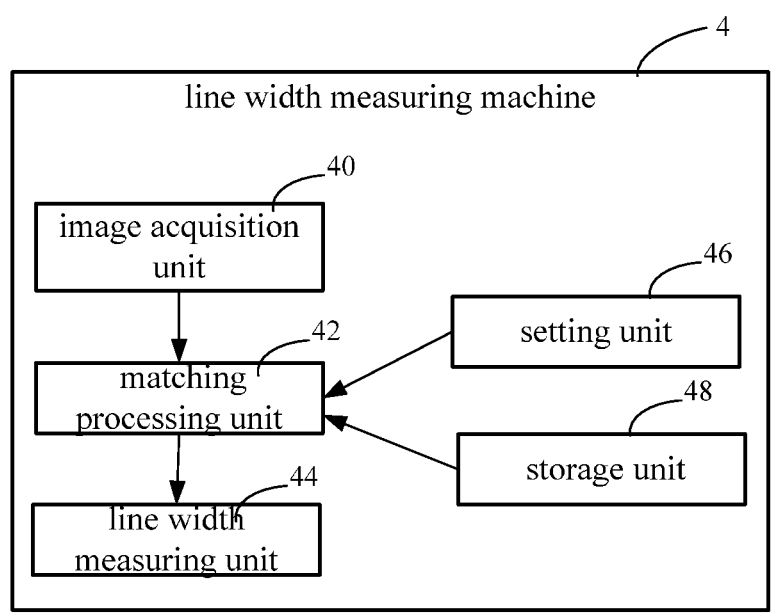
FIG. 2 is a schematic view illustrating the partial functional module of the line width measuring machine according to one embodiment of the present invention.

Accordingly, the embodiment of the present invention further provides a pattern matching apparatus, which is used for line width measuring machine, comprising the image acquisition unit and the matching processing unit. The functions of both can be found in the description from FIGS. 2 to 4 mentioned above and not repeated here.

One embodiment of the pattern matching method according to the present invention is illustrated accompanying FIG. 5 as follows.

The pattern matching method according to the present invention is used in measurement process for line width measuring machine, which comprises the steps as follows.

Read the standard pattern used for matching on the at least one predetermined position of the measured sample, the measured sample is the transparent substrate coated with multiple patterns, such as the standard pattern 30 in FIG. 3. The standard pattern represented by A in FIG. 5 has a certain degree of gray-scale.

Respectively compare each standard pattern A of the measured sample with prestored multiple designed original images corresponding to the standard pattern, and the difference within the multiple designed original images is the gray-scale, as shown in FIG. 5. For the standard pattern 30, it stores six corresponding designed original images (see B1-B2 in FIG. 5), wherein the six corresponding designed original images are the same, and the difference is that the gray-scales of each designed original image are different. The multiple designed original images are stored in advance; similarly, it also stores multiple designed original images corresponding to the standard patterns on the other positions in advance. In the present embodiment, it needs to respectively compare the read standard pattern A with the six designed original image B1-B2.

If the standard pattern on the measured sample successfully compares with at least one designed original image, determine that the pattern matching is successful, and proceed with the subsequent line width measurement process; otherwise, determine that the pattern matching is failed. Specifically, respectively compare the standard pattern A read from the measured sample with the corresponding designed original images (B1-B2). If at least one similarity reaches the predetermined ratio, determine that the comparison between the standard pattern on the measured sample and the designed original image is successful. The similarity reaching the predetermined ratio may be preset. For example, in one embodiment, the predetermined ratio may be 60%. As long as the ratio of both reaches to 60%, the comparison of both is successful. In the present embodiment, the similarity between the designed original image B4 and the standard pattern A reaches the predetermined ratio, so it can determine that the matching of the standard pattern and the designed original image is successful.

The embodiment according to the present invention has the beneficial effects as follow.

According to the embodiment of the present invention, it stores multiple designed original images for each standard pattern on the measured samples in advance, and the difference within the multiple designed original images is gray-scale; as long as the standard pattern on the measured sample successfully compares with at least one of the designed original image, determining that the pattern matching is successful. Then, it can proceed with the subsequent line width measurement process directly. In this way, it can improve the accuracy and the success rate of the pattern matching.

The preferred embodiments according to the present invention are mentioned above, which cannot be used to define the scope of the right of the present invention. Those modifications and variations are considered encompassed in the scope of protection defined by the claims of the present invention.

What is claimed is:

1. A pattern matching method of a pattern matching apparatus, which is used in measurement process for line width measuring machine, comprising:
   using an image acquisition unit to read a standard pattern used for matching on the at least one predetermined position of a measured sample, and the measured sample being a transparent substrate coated with multiple patterns;
   using a matching processing unit to compare each standard pattern of the measured sample with prestored multiple designed original images corresponding to the standard pattern, and the difference within the multiple designed original images being the gray-scale;
   comparing the standard pattern on the measured sample with each corresponding designed original image, determining that the comparison between the measured sample on the standard pattern and the designed original image is successful if a similarity of at least one reaches a predetermined ratio, wherein the similarity reaching the predetermined ratio can be preset; otherwise, determining that the pattern matching is failed.

2. The pattern matching method as claimed in claim 1, wherein it comprises: forming the standard pattern in advance on the at least one predetermined position of the measured sample.

3. The pattern matching method as claimed in claim 1, wherein it comprises: storing the designed original image in advance from each predetermined position, the designed original image corresponding to the standard pattern on each position being a plurality, and the gray-scale corresponding to each designed original image being different.

4. A pattern matching apparatus, which is used for line width measuring machine, comprising:
   an image acquisition unit, which is used to read a standard pattern used for matching on the at least one predetermined position of a measured sample, and the measured sample being a transparent substrate coated with multiple patterns;
   a matching processing unit, which respectively compares each standard pattern of the measured sample with prestored multiple designed original images corresponding to the standard pattern, and the difference within the multiple designed original images being the gray-scale; determining that the pattern matching is successful if the standard pattern on the measured sample successfully compares with at least one designed original image; and
   a storage unit, which is used to store the designed original image on each predetermined position, the designed original image corresponding to the standard pattern on each position being a plurality, and the gray-scale corresponding to each designed original image being different;
   wherein, the matching processing unit further comprises:
   an obtaining subunit, which obtains the multiple designed original images corresponding to the standard pattern on the measured sample from the storage unit;

a matching sub-unit, which respectively compares the standard pattern with the multiple designed original images obtained from the obtaining subunit; and a matching result judgment unit, which is used to determine that the comparison between the standard pattern on the measured sample and the designed original image is successful when the similarity between the standard pattern and one of the designed original images reaches the predetermined ratio; otherwise, determining that the comparison is failed.

5. The pattern matching apparatus as claimed in claim 4, wherein it further comprises:

a setting unit, which is used to set the similarity ratio between the standard pattern and the designed original image for the determination of the matching result judgment unit.

6. The pattern matching apparatus as claimed in claim 4, wherein the measured sample is the transparent substrate coated with multiple patterns, and the patterns contain multiple segments; at least one standard pattern is further coated at the predetermined position on the measured sample.

7. A line width measuring machine, comprising:

an image acquisition unit, which is used to read a standard pattern used for matching on the at least one predetermined position of a measured sample, and the measured sample being a transparent substrate coated with multiple patterns;

a matching processing unit, which respectively compares each standard pattern of the measured sample with pre-stored multiple designed original images corresponding to the standard pattern, and the difference within the multiple designed original images being the gray-scale; determining that the pattern matching is successful if the standard pattern on the measured sample successfully compares with at least one designed original image;

a line width measuring unit, which is used to measure the line width of the measured samples after the matching processing unit determines that the pattern matching is successful; and a storage unit, which is used to store the designed original image on each predetermined position, the designed original image corresponding to the standard pattern on each position being a plurality, and the gray-scale corresponding to each designed original image being different;

wherein, the matching processing unit further comprises:

an obtaining subunit, which obtains the multiple designed original images corresponding to the standard pattern on the measured sample from the storage unit;

a matching sub-unit, which respectively compares the standard pattern with the multiple designed original images obtained from the obtaining subunit; and a matching result judgment unit, which is used to determine that the comparison between the standard pattern on the measured sample and the designed original image is successful when the similarity between the standard pattern and one of the designed original images reaches the predetermined ratio; otherwise, determining that the comparison is failed.

8. The line width measuring machine as claimed in claim 7, wherein it further comprises:

a setting unit, which is used to set the similarity ratio between the standard pattern and the designed original image for the determination of the matching result judgment unit.

9. The line width measuring machine as claimed in claim 8, wherein the measured sample is the transparent substrate coated with multiple patterns, and the patterns contain multiple segments; at least one standard pattern is further coated at the predetermined position on the measured sample.

* * * * *